Feb. 26, 1974 L. E. GAVELLO Plant Pat. 3,495
HEBE (VERONICA) PLANT
Filed Oct. 19, 1972
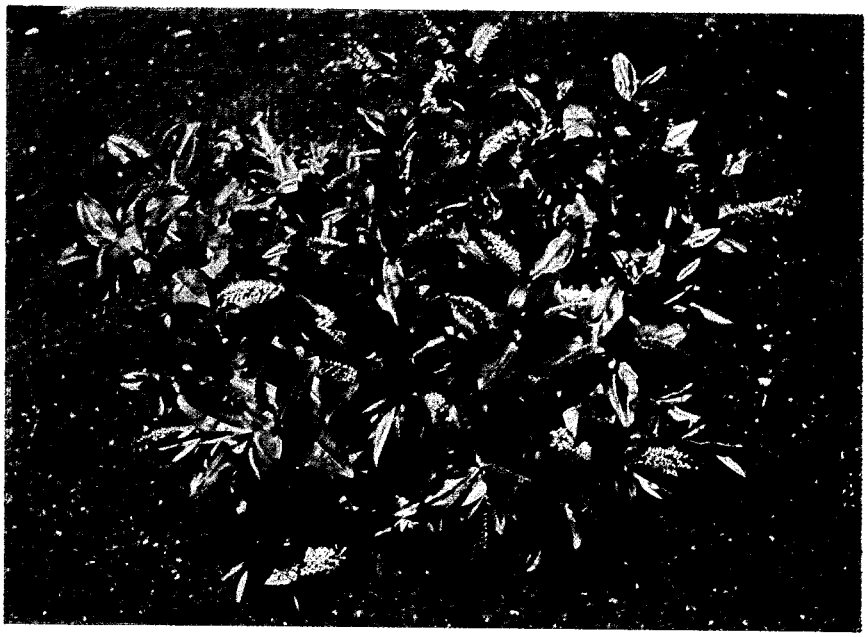
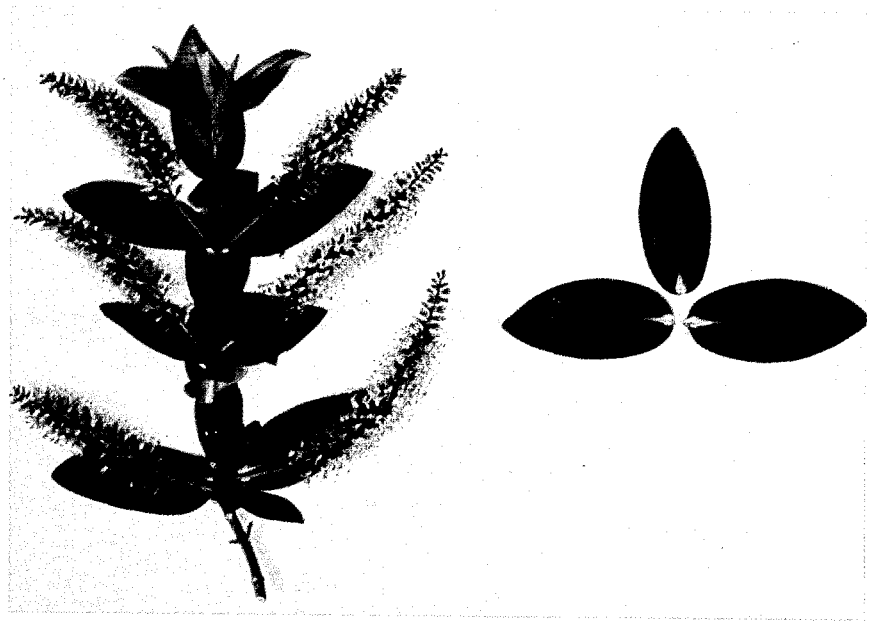

United States Patent Office

Plant Pat. 3,495
Patented Feb. 26, 1974

3,495

HEBE (VERONICA) PLANT

Louis E. Gavello, 3436 Maricopa Ave.,
Richmond, Calif. 94804

Filed Oct. 19, 1972, Ser. No. 299,122
Int. Cl. A01h *5/00*
U.S. Cl. Plt.—54 1 Claim My invention relates to a new and distinct variety of evergreen Hebe (Veronica) plant of shrub type which was initially originated by me as a selective seedling at my nursery at Richmond, Calif., and thereafter effectively reproduced by me from cuttings at the same location.

My new shrub is a cross between *Veronica Imperialis* and *Veronica Evansii*, neither of which is patented.

The accompanying drawing shows, in separate views, a typical shrub of my new variety of Veronica plant, a number of racemes on a branch, with some as yet unopened, and speciments of leaves, the views being depicted in color as nearly true as is reasonably possible to make the same in a color illustration of this character.

The primary distinctions of my new variety over the parent plants lie in the color and size of the blossoms, and the fact that it can not only be grown in standard form, but lends itself to being espallierd on trellises, or trained to grow flattened out against fences, walls or like structures. The shrub is a very good one for formation or group planting, as informal hedges, and in large planter boxes. It grows well in windy areas in full sun or partial shade.

My new Veronica plant represents a unique combination which is definitely different from that of any other variety of Veronica plant of which I am aware.

More specifically as to plant characteristics:

FORM

My new shrub grows to a height of approximately 4 feet and a width of approximately 4 feet. It is medium compact and normally of upright bush form.

FOLIAGE

Cossack green as identified by Plate 23–J11 on page 69 of Dictionary of Color, 1950, by Maerz and Paul.

Lanceolate to elliptic—2½ to 3½ inches in length and 1¼ to 1½ inches in width.

Glabrous, smooth, with a midrib prominent below, other veins being inconspicuous.

Leaf margins are entire, the leaves being shiny and duller below.

Nearly sessile, decussately arranged 1 to 1½ inches apart.

Stems are cylindrical, glabrous and of a color, matching Plate 56–12E of page 135 of the above Dictionary of Color, such plate identifying the color as Port.

FLOWERS

Pansy in color as identified by Plate 41–K12 of page 105 of the above Dictionary of Color.

Borne in axiallary racemes; loose at the base and denser about one third up, then tapering to the tip.

Racemes are approximately 6 inches long, 1½ inches wide, with about 150 flowers on each.

Lower 0–3 flowers subtended by foliaceous bracts. Other flowers subtended by subulate bractlets about 1/16 to ⅛ inches long.

Individual flowers are pedicels about ⅛ to 3/16 inches long, corollas being four lobed, three below and one above and about 3/16 inches wide and ¼ inches high.

Calyx is greenish, four toothed and about ⅛ inches long.

Stamens are two per flower, filaments are 1/16 inches long and whitish in color.

Anthers are purple with whitish pollen.

Styles are elongated in fruit, about ⅜ inches long and very slender.

Fruits are flattened and elliptical in shape, about 5/16 inches long and 3/16 inches wide, and smooth and shiny.

BLOOMING PERIOD

In the San Francisco Bay area, the plant has a blooming period from June until frost, most profuse blooming occuring from June until approximately the middle of August.

Having thus described my invention and discovery, I claim:

1. A new and distinct variety of Veronica plant substantially as herein described and characterized by its large blossoms as compared to its parent plants and the pansy color of said blossoms.

No references cited.

ROBERT E. BAGWILL, Primary Examiner